(12) United States Patent
Shigekawa et al.

(10) Patent No.: US 8,982,451 B2
(45) Date of Patent: Mar. 17, 2015

(54) PUMP PROBE MEASURING DEVICE

(75) Inventors: Hidemi Shigekawa, Ibaraki (JP);
Osamu Takeuchi, Ibaraki (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/236,771

(22) PCT Filed: Jul. 31, 2012

(86) PCT No.: PCT/JP2012/069517
§ 371 (c)(1),
(2), (4) Date: Apr. 25, 2014

(87) PCT Pub. No.: WO2013/018813
PCT Pub. Date: Feb. 7, 2013

(65) Prior Publication Data
US 2014/0240710 A1    Aug. 28, 2014

(30) Foreign Application Priority Data
Aug. 2, 2011 (JP) .................................. 2011-169682

(51) Int. Cl.
*G01N 21/55* (2014.01)
*G01N 21/17* (2006.01)
(Continued)

(52) U.S. Cl.
CPC ............ *G01N 21/55* (2013.01); *G01N 21/1717* (2013.01); *G01N 2021/1719* (2013.01);
(Continued)

(58) Field of Classification Search
USPC ......... 359/326, 331; 850/6, 21; 250/306, 310; 73/800
See application file for complete search history.

(56) References Cited

U.S. PATENT DOCUMENTS 5,373,381 A * 12/1994 Alfano et al. ................. 359/108
6,211,961 B1 * 4/2001 Maris ............................ 356/432
(Continued)

FOREIGN PATENT DOCUMENTS

JP    H06-307818 A    11/1994
JP    2008-139028 A    6/2008
(Continued)

OTHER PUBLICATIONS

International Search Report issued in Application No. PCT/JP2012/069517, mailed Sep. 4, 2012.
(Continued)

*Primary Examiner* — Daniel Petkovsek
(74) *Attorney, Agent, or Firm* — Rader, Fishman & Grauer PLLC

(57) ABSTRACT

A pump probe measuring device (1) comprises: an ultrashort optical pulse laser generator (2) for generating a first ultrashort optical pulse train which is a pump light (3a), second and third ultrashort optical pulse trains (3b), (3c) which are probe lights; an optical shutter unit (6) to which the second and the third ultrashort pulse trains (3b), (3c) are introduced; and a detecting unit (20) including an irradiation optical system (8) for directing the pump light (3a), the first probe light (3b) and the second probe light (3c) to a sample (7), a sensor (11) for detecting a probe signal from the sample (7), and a phase-sensitive detecting means (12) connected to the sensor (11). An optical shutter control unit (10) periodically modulates the delay time of the first probe light (3b) and that of the second probe light (3c) with respect to the pump light (3a), and the modulated first and second probe lights (3a), (3b) illuminate the sample (7) alternately to detect the probe signals from the sample (7) by the phase-sensitive detecting means (12) in synchronization with the periodic modulation signal of the delay time.

20 Claims, 11 Drawing Sheets

(51) Int. Cl.
*B82Y 35/00* (2011.01)
*G01Q 60/12* (2010.01)

(52) U.S. Cl.
CPC   *G01N2021/1725* (2013.01); *G01N 2021/1789* (2013.01); *H01J 2237/2818* (2013.01); *B82Y 35/00* (2013.01); *G01Q 60/12* (2013.01); *G01N 2201/0697* (2013.01); *G01N 2021/1791* (2013.01)
USPC .............................................. 359/331; 850/6

(56) References Cited

U.S. PATENT DOCUMENTS

| 7,230,708 | B2* | 6/2007 | Lapotko et al. ................ 356/432 |
| 7,961,379 | B2  | 6/2011 | Shigekawa et al. |

| 2003/0091116 | A1 | 5/2003 | Yap et al. |
| 2010/0088787 | A1 | 4/2010 | Shigekawa et al. |
| 2011/0109897 | A1 | 5/2011 | Bataillou et al. |

FOREIGN PATENT DOCUMENTS

| JP | 2008-139029 A | 6/2008 |
| TW | 200407586 A | 5/2004 |

OTHER PUBLICATIONS

Y. Terada et al., "Real-space imaging of transient carrier dynamics by nanoscale pump-probe microscopy", nature photonics vol. 4, Dec. 2010 (Published online on Oct. 24, 2010), pp. 869-874 (6 sheets), Macmillan Publishers Ltd.
Office Action issued in Taiwan Application No. 101127706, dated May 26, 2014.

* cited by examiner

Delay time

PUMP PROBE MEASURING DEVICE

TECHNICAL FIELD

The present invention relates to a pump probe measuring device.

BACKGROUND ART

To measure ultrafast phenomena that occur in picosecond (ps) to femtosecond (fs) regions, measurements using an ultrashort pulse laser are carried out widely. For example, in a pump probe reflectance measurement, a high-intensity pump pulse is focused to an object to be measured first to excite the sample instantaneously. Then, while the excited state is being relaxed, an irradiation of a low-intensity probe pulse is applied, and the intensity of the reflected light is measured. The measured intensity of the reflected light is proportional to the reflectance of the sample at the moment when it is hit by the probe pulse. By measuring the intensity of the reflected light while gradually changing the delay time of the probe pulse with respect to the pump pulse, change in the reflectance of the sample between before and after the excitation can be observed with the time resolution comparable to the duration of the laser pulse. This time resolution falls within a picosecond to femtosecond range.

Since the intensity of signals obtained by such ultrahigh-speed measurement is extremely weak in many cases, a modulation measurement is performed to improve the signal-to-noise ratio. As the most common method, the intensity of the pump pulse is modulated, and the response of the probe signal to this modulation is detected by using a lock-in amplifier. In addition, methods in which polarization of the light of the pump pulse or the delay time is modulated are also known.

It is especially noteworthy that the delay time modulation method, in which delay time is modulated as a rectangular wave, has recently been found to be effective in order to realize a time-resolved scanning probe microscope, which is a scanning probe microscope combined with a pulse laser. The time-resolved scanning probe microscope achieving 1-ps temporal resolution and 1-nm spatial resolution at the same time has thus been constructed.

To control the delay time of laser pulse precisely in a time domain from fs to nanosecond (ns), the length of optical path is generally varied.

FIG. 10 is a view illustrating the configuration of a conventional delay time modulation device. As shown in FIG. 10, the conventional delay time modulation device performs a periodic delay time modulation by mechanically vibrating the position of mirror. The laser pulse from the light source is divided by a half mirror 1 (HM1) into two optical paths, namely a path to a retroreflector 1 (RR1) and that to a retroreflector 2 (RR2). It is not necessary that the amount of light at dividing is 1:1. Any ratio can be selected arbitrarily depending on the property of the half mirror to be used. RR1 and RR2 are devices that reflect optical pulses in a direction directly opposite to the incident direction. Retroreflectors usually composed of three mirrors placed so that they make right angles to one another are generally used. The reflected lights from RR1 and RR2 are overlapped precisely on the same optical axis at a half mirror 2 (HM2).

When the length of the optical path passing through RR1 differs from that of the optical path passing through RR2, optical pulses appear at different positions temporally deviated from each other on the optical axis overlapped at HM2. The delay time between the two pulses can be controlled precisely by mechanically varying the position of RR1 or RR2. By using a piezoelectric device, etc., the accuracy of 1 fs or shorter can be achieved. To modulate the delay time periodically using such a device, it is only necessary to periodically change the position of RR1, for example. So far, many measurements have been carried out wherein the mirror position is varied periodically to perform the delay time modulation as described above.

However, the device as shown in FIG. 10 has major limitations in the amplitude of modulation and in the frequency of modulation. The optical path length and the delay time are proportional to each other, with the velocity of light serving as the coefficient. For example, the position of the mirror must be varied with the amplitude of 1.5 cm to modulate the delay time by 100 ps. Such a significant modulation in the mirror position can be achieved only at an extremely low frequency of approximately 10 Hz. In using an amplitude about 1.5 cm or more, or a frequency about 10 Hz, problems may arise. The mechanical vibration may be generated and give bad influences to the optical device located around. It becomes impossible to realize the accurate modulation due to the deformation of the driving mechanism itself.

Meanwhile, since the result of the modulation performed at such a low frequency is strongly affected by the fluctuation in the intensity of laser light, etc., the time-resolved measurement with modulating mirror position is only useful when the modulation amplitude is very small (of up to about 100 fs).

Recently, following the development of a time-resolved scanning probe microscope, which is a scanning probe microscope adopting delay time modulation of a pulse laser, a delay time modulation method using high speed optical shutters (called pulse pickers) capable of passing or blocking optical pulses with respect to each pulse has been proposed, and its usefulness has been confirmed (Patent Literature 1).

FIG. 11 is a time chart illustrating the conventional delay time modulation method using pulse pickers.

A laser oscillator generates laser pulses at time intervals of approximately 10 ns, and these laser pulses are split into two optical paths by a half mirror, etc., and are introduced to respective two pulse pickers from the right-hand side. The pulse picker can selectively transmit one optical pulse at arbitrary timing from the continuous pulse train.

It is therefore possible, as shown in FIG. 11, to generate a delay time by transmitting pulses at different timing. When the delay time is generated by using pulse pickers as described above, the delay time modulation can be performed at extremely high speed and with large amplitude. In the first place, with this method, the minimum value of the amplitude of the modulation delay time is determined by the pulse interval of the optical pulse train, and typically it is approximately 10 ns. This value is equivalent to approximately 3 m in the length of optical path, which is 3 to 4 orders greater than that of the amplitude of the delay time modulation achievable by changing mirror positions. Furthermore, the delay time can be changed for each transmission pulse with this method. Thus, approximately 1 MHz high-speed modulation can be performed as required.

Meanwhile, the delay time modulation using pulse pickers as shown in FIG. 11 cannot produce favorable results when applied to observing fast phenomena of 1 ns or faster. This is because that pulses are picked to generate delay time, thus causing the excitation frequency of the sample, namely the number of times of measurement per unit time, to decrease significantly.

When water-cooled type Pockels cells are used as pulse pickers, for example, it is difficult to increase the repetition frequency of the output optical pulses to higher than 2 MHz due to the restriction imposed by the generation of heat from the Pockels cells. Whereas the repetition frequency of the conventional titanium-sapphire laser oscillator is generally close to 100 MHz, the number of times of excitation of the sample per unit time becomes 1/50, and also the number of detected signals becomes 1/50, when pulse pickers are used.

CITATION LIST

Patent Literature

Patent Literature 1: JP 2008-139029 A

Non-Patent Literature

Y. Terada, S. Yoshida, O. Takeuchi and H. Shigekawa, "Real space imaging of carrier dynamics by nanoscale pump-probe microscopy", Nature Photonics DOI:10.1038/NPHOTON.2010.235 (2010)

SUMMARY OF INVENTION

Technical Problem

The problem of the conventional pump probe measuring device is that the high-sensitivity measurement cannot be performed when it is used to measure fast phenomena.

In consideration of the problem described above, an object of the present invention is to provide a pump probe measuring device capable of measuring fast phenomena of 1 ns or faster with high accuracy.

Solution to Problem

To solve the above problem, the present invention provides a pump probe measuring device including: an ultrashort optical pulse laser generator for generating a first ultrashort optical pulse train which is a pump light, a second ultrashort optical pulse train, which has a first delay time with respect to the pump light and is a probe light, and a third ultrashort optical pulse train, which has a second delay time with respect to the pump light and is a probe light; an optical shutter unit to which the second and the third ultrashort optical pulse trains are introduced; an optical shutter control unit for controlling the optical shutter unit; an irradiation optical system for irradiating a sample with the pump light and the probe lights; and a detecting unit including a sensor for detecting probe signals from the sample and a phase-sensitive detecting means connected to the sensor, wherein the second ultrashort optical pulse train and the third ultrashort optical pulse train illuminate the sample alternately as the probe light, controlled by the optical shutter control unit, to modulate the delay times of the probe lights with respect to the pump light periodically, thereby detecting the probe signals by the phase-sensitive detecting means with synchronized to the periodic modulation of the delay time.

In the above configuration, the ultrashort optical pulse laser generator may include: an ultrashort optical pulse laser light source; an optical element that divides an ultrashort optical pulse generated by this ultrashort optical pulse laser light source into three to form a first ultrashort optical pulse train which is the pump light, and second and third ultrashort optical pulse trains which are the probe lights; a first optical delay unit for delaying the second ultrashort optical pulse train with respect to the pump light by a first delay time; and a second optical delay unit for delaying the third ultrashort optical pulse train with respect to the pump light by a second delay time.

The ultrashort optical pulse laser generator may also include: a first ultrashort optical pulse laser light source for generating the pump light; a second ultrashort optical pulse laser light source for generating a second ultrashort optical pulse train which is the probe light; and a third ultrashort optical pulse laser light source for generating a third ultrashort optical pulse train which is the probe light, wherein the first to the third ultrashort optical pulse laser light sources may oscillate synchronously with specified delay times.

The optical shutter unit includes: a first optical shutter; and a second optical shutter, wherein the second ultrashort optical pulse train may be introduced to the first optical shutter, and the third ultrashort optical pulse train may be introduced to the second optical shutter.

The optical shutter unit may include only one optical shutter that has an electrooptic element and a polarization rotation element, wherein the second and the third ultrashort optical pulse trains may be introduced to the optical shutter unit.

The pump probe measuring device may further include: a first optical delay unit for delaying the second ultrashort optical pulse train with respect to the pump light by the first delay time; and a second optical delay unit for delaying the third ultrashort optical pulse train with respect to the pump light by the second delay time.

The sensor may be comprised of a photodiode, and a reflected light of the probe light at the sample may be introduced to the photodiode, and an intensity of the reflected light may be detected as a first probe signal.

The sensor may be comprised of a scanning probe microscope, and a second probe signal may be detected by a probe of the scanning probe microscope on a surface of the sample, to which the pump light and the probe lights are focused.

A measuring device according to the present invention includes any one of the above-mentioned pump probe measuring devices.

Advantageous Effects of Invention

According to the present invention, in a time-resolved measurement using a pulse laser covering a femtosecond region, faint signals can be measured highly sensitively, accurately, and stably in a wide measurement range including phenomena having short to long relaxation time, without modulating the intensity of illuminating light or picking pulses using pulse pickers. According to the present invention, a pump probe measuring device for measuring and analyzing ultrafast physical phenomena on the order of ps, 1 ns or faster for example, can be provided along with a time-resolved scanning probe microscope using this measuring device.

Figure 1:
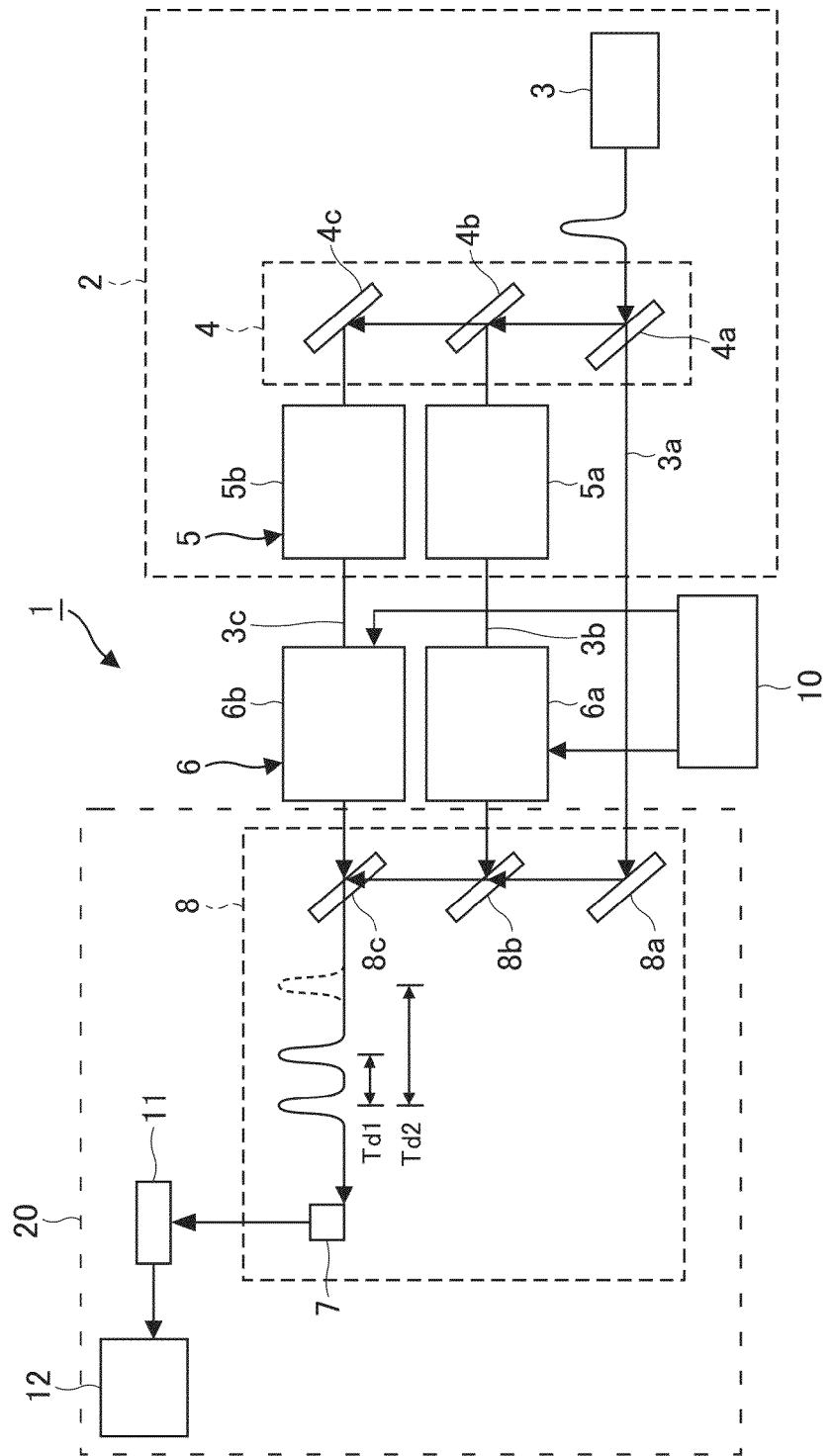
FIG. 1 is a view illustrating a typical configuration of a pump probe measuring device according to a first embodiment of the present invention.

REFERENCE SIGNS LIST 1, 30, 40: Pump probe measuring device
2, 2A: Ultrashort optical pulse laser generator
3: Laser light source
3a: Pump light
3b: First probe light
3c: Second probe light
4: Branch optical system
4a and 4b: Half mirror
4c: Mirror
5: Optical delay unit
6, 6A: Optical shutter unit
6a, 6b, 6c: Pockels cell
6d: Mirror
6e: Half mirror
7: Sample
8, 8A: Irradiation optical system
8a: Mirror
8b, 8c: Half mirror
10: Optical shutter control unit
11: Sensor
12: Phase-sensitive detecting means
15: Probe
16: DC power supply
17: Current meter
20: Detecting unit
31: Polarization rotation element (½λ plate)
43: Laser light source

DESCRIPTION OF EMBODIMENTS

The embodiments of the present invention will hereinafter be described in detail by referring to drawings.

First Embodiment

FIG. 1 is a view illustrating a typical configuration of a pump probe measuring device 1 according to the first embodiment of the present invention. As shown in FIG. 1, the pump probe measuring device 1 includes: an ultrashort optical pulse laser generator 2 for generating a first ultrashort optical pulse train which is a pump light 3a, a second ultrashort optical pulse train, which is a first probe light 3b, and a third ultrashort optical pulse train which is a second probe light 3c; an optical shutter unit 6 to which the second and the third ultrashort optical pulse trains are introduced; an optical shutter control unit 10 for controlling the optical shutter unit 6; an irradiation optical system 8 for directing the pump light 3a and the probe lights 3b, 3c to a sample; and a detecting unit 20 including a sensor 11 for detecting a probe signal from the sample 7 and a phase-sensitive detecting means 12 for detecting the probe signal.

The ultrashort optical pulse laser generator 2 generates the first ultrashort optical pulse train which is the pump light 3a, the second ultrashort optical pulse train, which has a first delay time with respect to the pump light 3a and is the first probe light 3b, and the third ultrashort optical pulse train, which has a second delay time with respect to the pump light and is the second probe light 3c.

The ultrashort optical pulse laser generator 2 includes: a laser light source 3; a branch optical system 4; and an optical delay unit 5. The branch optical system 4, which is comprised of optical elements, branches the laser light from the laser light source 3 into the pump light 3a, the first probe light 3b, and the second probe light 3c.

The laser light source 3 is a femtosecond pulse laser light source, for example. Specifically, a titanium-sapphire laser oscillator can be used as the laser light source, which generates laser pulses having wavelength of approximately 800 nm and time width of approximately 25 fs at repetition frequency of approximately 100 MHz, and average brightness of approximately 1 W.

The branch optical system 4 includes: a first half mirror 4a to which the light from the laser light source 3 is introduced; a second half mirror 4b, which is installed on the optical path of the reflected light from the first half mirror 4a; and a first mirror 4c, which is installed on the optical path of the light penetrating the second half mirror 4b.

The second half mirror 4b is placed above the first half mirror 4a. The first mirror 4c is placed above the second half mirror 4b.

In the branch optical system 4, the laser pulse from the laser light source 3 is branched into a transmitted light and a reflected light by the first half mirror 4a placed on the optical path of the laser pulse emitted from the laser light source 3. Here, the transmitted light from the half mirror 4a is used as the pump light 3a, whereas the reflected light is used as the first and the second probe lights 3b, 3c.

The second half mirror 4b, which is placed on the optical path of the reflected light from the first half mirror 4a, branches this reflected light into a transmitted light and a reflected light, allowing the reflected light to serve as a second ultrashort optical pulse train, and the transmitted light as a third ultrashort optical pulse train.

The optical delay unit 5 includes: a first optical delay unit 5a to which the second ultrashort optical pulse train reflected by the second half mirror 4b is introduced; and a second optical delay unit 5b to which the third ultrashort optical pulse train penetrating the second half mirror 4b and then reflected by the first mirror 4c is introduced. The first and the second optical delay units 5a, 5b can be configured using an optical system of publicly known structure that adjusts optical path length using movable mirrors. For example, the movable mirrors are a pair of reflecting mirrors placed obliquely at an angle of 45 degrees with the incident light axis. The light entering along the incident light axis is reflected by one of the reflecting mirrors in a direction perpendicular to the incident light axis, introduced to the other reflecting mirror, and reflected by that reflecting mirror in a direction parallel to the incident direction.

The movable mirrors are thus moved in the direction of the optical axis for adjustment, allowing the length of the optical path to be adjusted. Accordingly, by moving the movable mirrors, the first optical delay unit 5a emits the first probe light 3b having a first delay time with respect to the first ultrashort optical pulse train which is the pump light 3a, to the optical shutter unit 6. Generally, the movable range of the optical path length of movable mirrors is approximately 30 cm, which provides delay time setting range of 0 to 1 ns between the pump light 3a and the first probe light 3b.

Similarly, with the second optical delay unit 5b, the second delay time of the second probe light 3c with respect to the pump light 3a can be set by moving the movable mirrors.

As described above, the ultrashort optical pulse laser generator 2 generates, from the laser light emitted from the laser light source 3, the first ultrashort optical pulse train which is the pump light 3a; the second ultrashort optical pulse train, which has delay time $T_{d1}$ with respect to the pump light 3a and is the first probe light 3b; and the third ultrashort optical pulse train, which has delay time $T_{d2}$ with respect to the pump light 3a and is the second probe light 3c.

The optical shutter unit 6 includes: a first optical shutter 6a to which the second ultrashort optical pulse train, which is the first probe light 3b, is introduced; and a second optical shutter 6b to which the third ultrashort optical pulse train, which is the second probe light 3c, is introduced. The optical shutter unit 6 is controlled by the optical shutter control unit 10. A delay time modulation is performed by opening the optical shutters 6a, 6b alternately. As the first and the second optical shutters 6a, 6b, an acoustooptic modulator (AOM) or an electrooptic modulator (EOM) can be used. As the electrooptic modulator, Pockels cells can be used. By using Pockels cells as the first and the second optical shutters 6a, 6b, a high-speed modulation of 1 kHz or higher i.e. high frequency modulation can be performed without involving a mechanical vibration, etc.

The optical shutter control unit 10 includes a function generator and an inverter, for example. The function generator generates a 1 kHz rectangular wave signal, and the output is sent to the first optical shutter 6a. The inverter reverses the sign of the signal from the functional generator, and the output is sent to the second optical shutter 6b. This configuration allows the first optical shutter 6a and the second optical shutter 6b to be opened alternately at intervals corresponding to 1 kHz frequency, for example.

The detecting unit 20 includes: an irradiation optical system 8; a sensor 11 for measuring probe signals obtained from reflected lights, etc. of the probe pulse lights 3b, 3c illuminating the sample 7; and a phase-sensitive detecting means 12 for detecting the dependency of the probe signals on delay times.

The irradiation optical system 8 has the function of focusing the pump light 3a generated from the ultrashort optical pulse laser generator 2, the first probe light 3b having the first delay time with respect to the pump light 3a, and the second probe light 3c having the second delay time with respect to the pump light 3a, on the sample 7. The irradiation optical system 8 as shown in FIG. 1 includes a second mirror 8a and two half mirrors 8b, 8c. The irradiation optical system 8 may further include a mirror or an objective lens for guiding the pump light 3a, the first probe light 3b, and the second probe light 3c to the surface of the sample 7, respectively. The pump light 3a, the first probe light 3b, and the second probe light 3c can thus be focused on the surface of the sample 7.

When the intensity of the reflected light is measured as the probe signal, the sensor 11 may be configured using a Si photodiode, for example. As the photodiode, a pin photodiode can be used. The probe light reflected by the sample 7 is introduced to the pin photodiode, and the intensity of the obtained reflected light can be measured as the probe signal.

As the phase-sensitive detecting means 12, a dual-phase lock-in amplifier can be used. By inputting the probe signal into the dual-phase lock-in amplifier, and performing a phase-sensitive detection at the delay time modulation frequency in the shutter control unit 10, the dependency of the probe signal from the sample 7 on the delay time can be measured by the sensor 11.

First, the optical path of the pump light 3a from the laser light source 3 to the sample 7 will be described.

The light from the laser light source 3 penetrates the first half mirror 4a, is reflected by the second mirror 8a, and then penetrates the third half mirror 8b. This transmitted light is reflected by the fourth half mirror 8c and is the pump light 3a to be introduced to the sample 7.

The first probe light 3b from the laser light source 3 to the sample 7 will then be described.

The light reflected by the first half mirror 4a, of the light coming from the laser light source 3, is divided into a transmitted light and a reflected light by the second half mirror 4b. On the optical path of this reflected light, the first optical delay unit 5a, the first optical shutter 6a, and the third half mirror 8b are placed.

Consequently, the light reflected by the first half mirror 4a and then by the second half mirror 4b, of the light from the laser light source 3, passes through the first optical delay unit 5a and the first optical shutter 6a, is reflected by the third half mirror 8b and then by the fourth half mirror 8c, and is the first probe light 3b, which is guided to the sample 7. The first optical delay unit 5a causes a delay time $T_{d1}$ to occur to the first probe light 3b, which is thus allowed to reach the sample 7 when $T_{d1}$ has elapsed since the pump light 3a reaches.

The second probe light 3c from the laser light source 3 to the sample 7 will then be described.

The light having penetrated the second half mirror 4b, of the light from the laser light source 3, is reflected by the first mirror 4c. On the optical path of this reflected light, the second optical delay unit 5b, the second optical shutter 6b, and the fourth half mirror 8c are placed.

Consequently, the light that is reflected by the first half mirror 4a and then penetrates the second half mirror 4b, of the light from the laser light source 3, is reflected by the first mirror 4c, penetrates the second optical delay unit 5b and the second optical shutter 6b, penetrates the fourth half mirror 8c, and then is guided to the sample 7 as the second probe light 3c. The second optical delay unit 5b causes a delay time $T_{d2}$ to occur to the second probe light 3c, which is thus allowed to reach the sample 7 when $T_{d2}$ has elapsed since the pump light 3a reaches.

Figure 2:
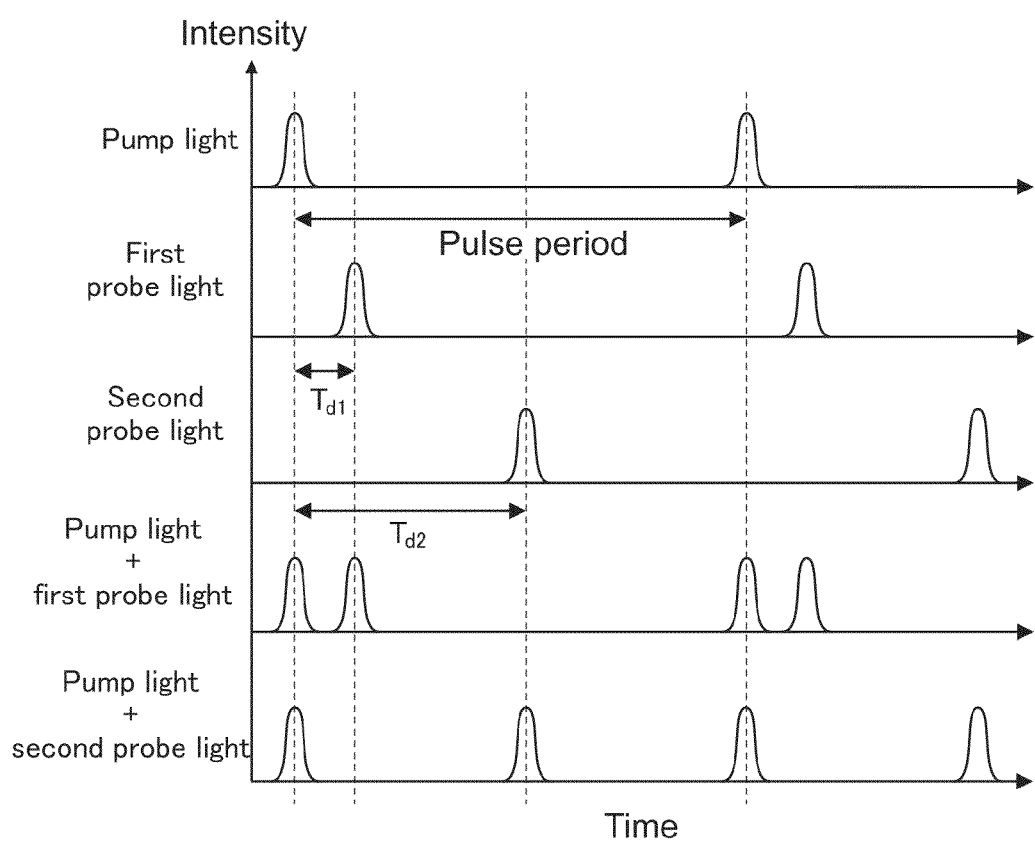
FIG. 2 is a time chart illustrating the relation among a pump light, a first probe light, a second probe light, the pump light plus the first probe light illuminating the sample, and the pump light plus the second probe light illuminating the sample.

FIG. 2 is a time chart illustrating the relation among the pump light 3a, the first probe light 3b, the second probe light 3c, the pump light 3a and the first probe light 3b impinging on the sample 7, and the pump light 3a and the second probe light 3c impinging on the sample 7.

The horizontal axis in FIG. 2 represents time. The vertical axis represents, from top to bottom, the intensity of the pump light 3a; that of the first probe light 3b, that of the second probe light 3c; that of the incident light (delay time: $T_{d1}$) illuminating the sample 7 when the first probe light 3b only is made to pass by the optical shutter unit 6; and that of the incident light (delay time: $T_{d2}$) illuminating the sample 7 when the second probe light 3c only is made to pass by the optical shutter unit 6.

As shown in FIG. 2, the optical shutter unit 6 allows either the first probe light 3b or the second probe light 3c only to be introduced to the sample 7. Consequently, the incident light to the sample 7 consists of a pulse pair having the delay time $T_{d1}$ when the first probe light 3b is introduced, and a pulse pair having the delay time $T_{d2}$ when the second probe light 3c is introduced.

Figure 3:
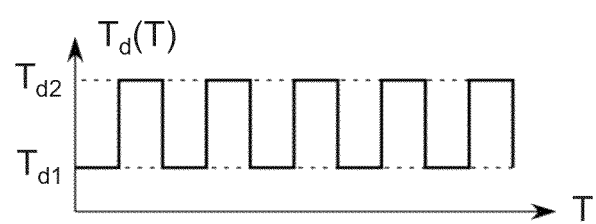
FIG. 3 is a time chart illustrating the time change in delay time.

FIG. 3 is a time chart illustrating the time change in delay time ($T_d$). As shown in FIG. 3, by switching the optical shutter unit 6 periodically, the delay time of the probe light is modulated between $T_{d1}$ and $T_{d2}$, following the form of a rectangular wave.

Figure 4:
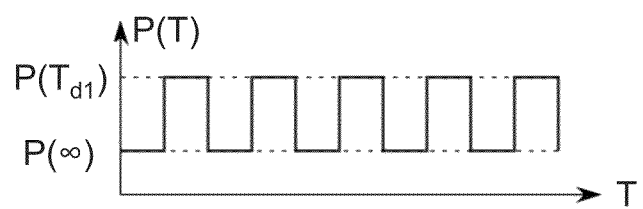
FIG. 4 is a time chart illustrating the signal measured by the detecting unit, namely the probe signal (P).

FIG. 4 is a time chart illustrating the temporal change of the probe signal (P) measured by the sensor 11. As shown in FIG. 4, the probe signal measured by the sensor 11 in accordance with a periodic modulation of the delay time is in a form of a rectangular wave signal vibrating between $P(T_{d1})$ and $P(T_{d2})$.

As a result of the probe signal vibrating in a form of a rectangular wave being input to the phase-sensitive detecting means 12, the measurement value obtained by the phase-sensitive detecting means 12 is proportional to the difference between probe signals $P(T_{d1})$ and $P(T_{d2})$ that correspond to the delay time of $T_{d1}$ and $T_{d2}$, respectively, namely $P(T_{d1})-P(T_{d2})$.

Figure 5:
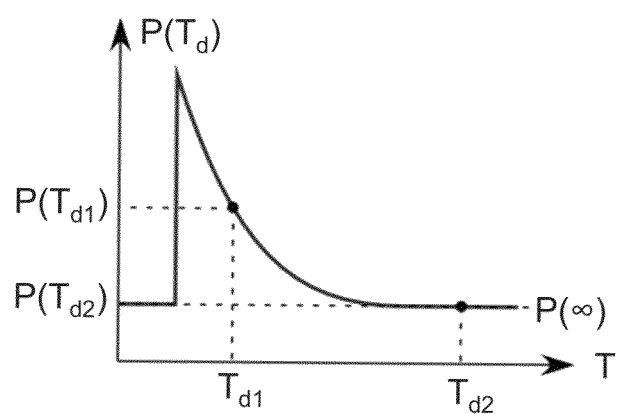
FIG. 5 is a chart illustrating the dependency of the probe signal (P) on delay time $T_d$.

FIG. 5 is a chart showing the dependency of the probe signal (P) on delay time $T_d$. As shown in FIG. 5, since the dependency of the probe signal on delay time $P(T_d)$ for large $T_d$ value, generally becomes asymptotic to the equilibrium value of P, namely $P(\infty)$, especially when a large delay time $T_{d2}$ is adopted, the measurement value can be regarded approximately as $P(T_{d1})-P(\infty)$. In this case, the measurement value becomes proportional to $P(T_{d1})$ itself, which is the value measured with reference to $P(\infty)$.

By using the pump probe measuring device 1 of the present invention, the dependency of the probe signal on delay time can thus be measured highly accurately for ultrafast phenomena of 1 ns or faster, namely on the order of ps.

The typical pulse repetition frequency, the pulse repetition period, 2 delay times, and the delay time modulation frequency are shown below.

Pulse repetition frequency: 100 MHz
Pulse repetition period: 10 ns
2 delay times: 0 to 5 ns
Delay time modulation frequency (opening/closing frequency of the shutter): 1 kHz (period: 1 ms)

Second Embodiment

Figure 6:
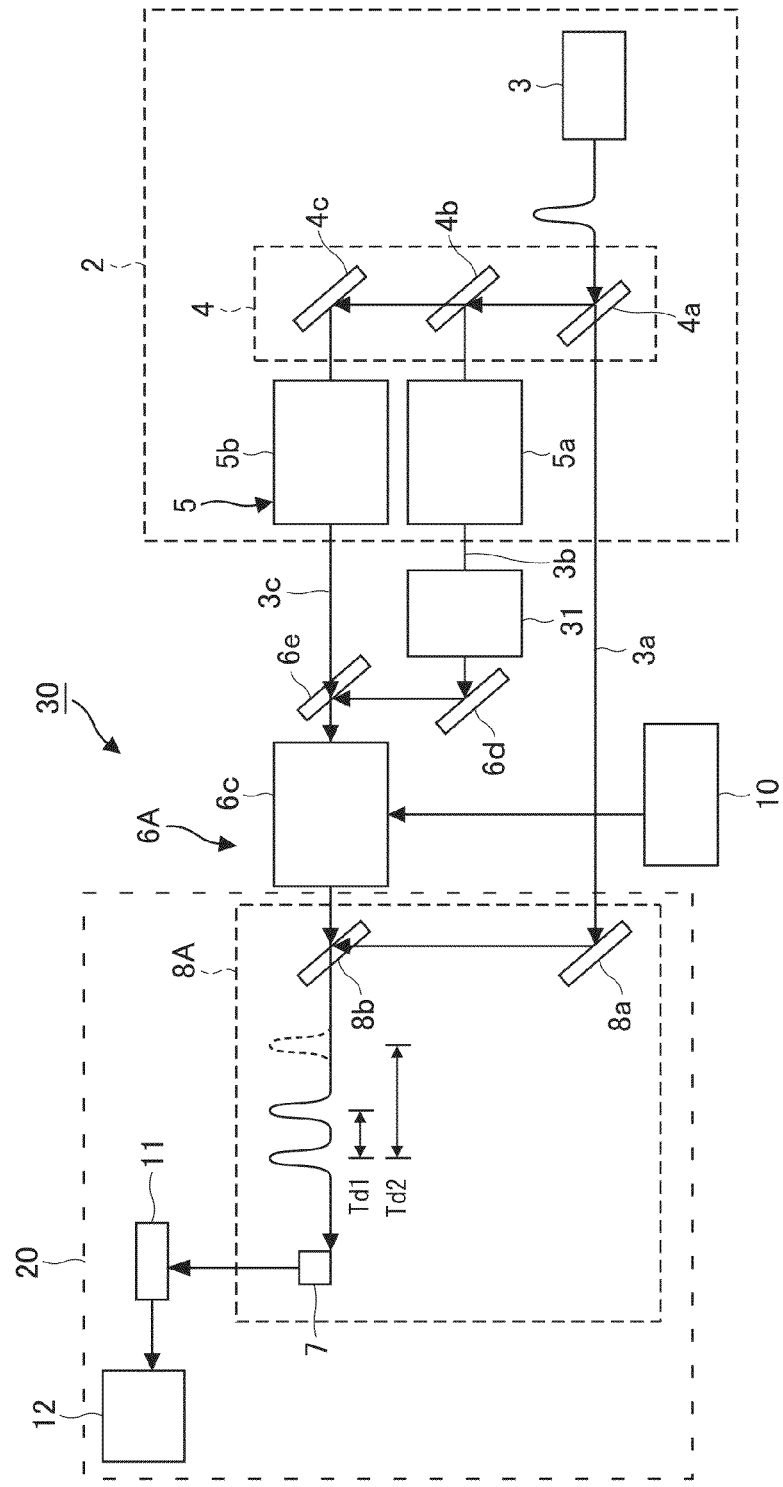
FIG. 6 is a view illustrating a typical configuration of a pump probe measuring device according to a second embodiment of the present invention.

FIG. 6 is a schematic view illustrating the configuration of a pump probe measuring device 30 according to a second embodiment of the present invention. As shown in FIG. 6, the pump probe measuring device 30 according to the second embodiment of the present invention differs from the pump probe measuring device 1 according to the first embodiment in that an optical shutter unit 6A is provided instead of the optical shutter unit 6 as shown in FIG. 1. The optical shutter unit 6A includes: a Pockels cell, which functions as an optical shutter 6c; a fifth half mirror 6e; a polarization rotation element 31; and a third mirror 6d. The irradiation optical system 8A includes the second mirror 8a and the third half mirror 8b. In other words, the number of half mirrors used in the irradiation optical system 8A in this embodiment is one less than that of the irradiation optical system 8 as shown in FIG. 1. The optical shutter control unit 10 has a circuit for generating 1 kHz rectangular wave, for example, as the signal for controlling the Pockels cell, which functions as the optical shutter 6c. As the optical shutter control unit 10, a pulse generator or the function generator can be used. The following description of FIG. 6 assumes that the optical shutter 6c is the Pockels cell.

First, the optical path of the pump light 3a from the laser light source 3 to the sample 7, will be described. The light from the laser light source 3 penetrates the first half mirror 4a, is reflected by the second mirror 8a, and then by the third half mirror 8b, and is the pump light 3a that is to be introduced to the sample 7.

The optical path of the first probe light 3b from the laser light source 3 to the sample 7, will then be described. The light reflected by the first half mirror 4a, of the light from the laser light source 3, is divided into a transmitted light and a reflected light by the second half mirror 4b. On the optical path of this reflected light, the first optical delay unit 5a, the polarization rotation element 31, and the third mirror 6d are placed. As the polarization rotation element 31, a ½ λ plate can be used. The ½λ plate 31 is also called a half-wave plate.

Accordingly, the light reflected by the first half mirror 4a, and then by the second half mirror 4b, of the light from the laser light source 3, penetrates the first optical delay unit 5a and the ½λ plate 31, is reflected by the third mirror 6d, and then by the fifth half mirror 6e, penetrates the Pockels cell 6c, and is introduced to the sample 7 as the first probe light 3b. The delay time $T_{d1}$ is generated to this first probe light 3b by the first optical delay unit 5a. Thus, the first probe light 3b reaches to the sample 7 when $T_{d1}$ has elapsed since the pump light 3a reaches to the sample 7.

Next, the optical path of the second probe light 3c from the laser light source 3 to the sample 7 will be described.

The light having penetrated the second half mirror 4b, of the light from the laser light source 3, is reflected by the first mirror 4c. On the optical path of this reflected light, the second optical delay unit 5b, the fifth half mirror 6e, the Pockels cell 6c, and the third half mirror 8b are placed. Accordingly, the light having been reflected by the first half mirror 4a and then having penetrated the second half mirror 4b, of the light from the laser light source 3, is reflected by the first mirror 4c, penetrates the second optical delay unit 5b, the fifth half mirror 6e, the Pockels cell 6c, and the third half mirror 8b, and then is introduced to the sample 7 as the second probe light 3c. The delay time $T_{d2}$ is generated to this second probe light 3c by the second optical delay unit 5b. Thus, the second probe light 3c reaches the sample 7 when $T_{d2}$ has elapsed since the pump light 3a reaches the specimen 7.

When the Pockels cell 6c does not allow a light having a certain polarization direction to pass, namely when it blocks that light, the light in the polarization direction, which is orthogonal to the direction of the blocked light, penetrates the element with little loss. Conversely, when the light having a certain polarization direction is allowed to pass with little loss, the light in the direction orthogonal to the direction of that light is blocked.

Hence, when the polarization direction of the second pulse train and that of the third pulse train are made to cross orthogonal to each other by placing the polarization rotation element 31 such as the ½λ plate, opening the Pockels cell 6c to the second pulse train means that the Pockels cell 6c is automatically closed to block the third pulse train. Conversely, closing the Pockels cell 6c to block the second pulse train means that the Pockels cell 6c is automatically opened to pass the third pulse train. In spite that the pump probe measuring device 30 as shown in FIG. 6 has only one Pockels cell 6c functioning as the optical shutter, unlike the pump probe measuring device 1 as shown in FIG. 1, which requires two optical shutters 6a, 6b, the same operation as the pump probe measuring device 1 can be ensured.

According to the pump probe measuring device 30, by placing the ½λ plate 31 after one of the optical delay unit 5a of the pump probe measuring device 1, and by rotating the polarization direction by 90 degrees, the quantity of the Pockels cells 6c to be used can be decreased to only one.

Furthermore, according to the pump probe measuring device 30, the technical difficulty of the pump probe measuring device 1, namely operating the two optical shutters 6a, 6b by temporally synchronizing them highly accurately, can be eliminated.

Third Embodiment

Figure 7:
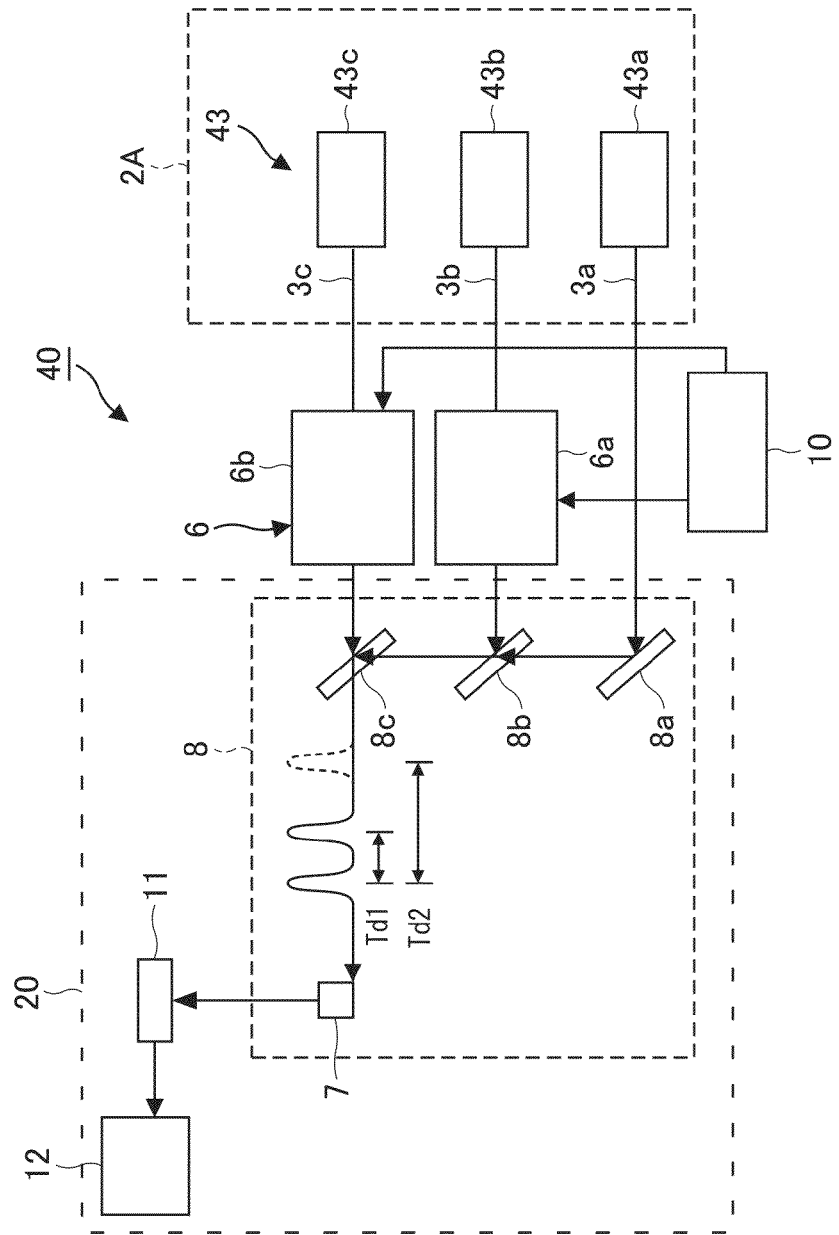
FIG. 7 is a view illustrating a typical configuration of a pump probe measuring device according to a third embodiment of the present invention.

FIG. 7 is a schematic view illustrating the configuration of a pump probe measuring device 40 according to a third embodiment of the present invention. As shown in FIG. 7, the pump probe measuring device 40 according to the third embodiment differs from the pump probe measuring device 1 according to the first embodiment in that an ultrashort optical pulse laser generator 2A is provided, instead of the above-mentioned ultrashort optical pulse laser generator 2. The ultrashort optical pulse laser generator 2A includes three laser light sources 43, namely a first laser light source 43a for generating a pump light 3a, a second laser light source 43b for generating a first probe light 3b, and a third laser light source 43c for generating a second probe light 3c.

First, the optical path of the pump light 3a from the first laser light source 43a to the sample 7 will be described. The light from the first laser light source 43a is reflected by the mirror 8a, penetrates the third half mirror 8b, is then reflected by the fourth half mirror 8c, and is the pump light 3a to be introduced to the sample 7.

Next, the optical path of the first probe light 3b from the second laser light source 43b to the sample 7 will be described. The second laser light source 43b is a laser light source that is synchronized with the first laser light source 43a, and oscillates when the delay time $T_{d1}$ has elapsed after the first laser light source 43a oscillates. The pulse light generated by the second laser light source 43b penetrates the first optical shutter 6a, is reflected by the third half mirror 8b, and then by the fourth half mirror 8c, and then introduced to the sample 7 as the first probe light 3b. The first probe light 3b reaches the sample 7 when $T_{d1}$ has elapsed since the pump light 3a illuminates the sample 7.

Next, the optical path of the second probe light 3c from the third laser light source 43c to the sample 7 will be described. The third laser light source 43c is a laser light source that is synchronized with the first laser light source 43a, and oscillates when delay time $T_{d2}$ has elapsed after the first laser light source 43a oscillates. The pulse light generated by the third laser light source 43c penetrates the second optical shutter 6b, and then the fourth half mirror 8c, and is guided to the sample 7 as the second probe light 3c. The second probe light 3c reaches the sample 7 when $T_{d2}$ has elapsed since the pump light 3a reaches the sample 7.

According to the pump probe measuring device 40, the optical delay unit 5 is not required because a plurality of laser light sources 43 are made to oscillate synchronously.

According to the pump probe measuring devices 1, 30, 40 of the present invention, pulses from the laser oscillator can be used for measurement without picking any of them, and the delay time modulation can be achieved at large amplitude and high frequency. Accordingly, a photocarrier excitation of the sample 7 and its relaxation process can be measured highly sensitively.

Fourth Embodiment

In the first to the third embodiments, the sensor 11 for detecting the probe signal from the sample 7 detects the reflected light from the sample 7 using the photodiode. Another embodiment in which a scanning probe microscope placed on the sample 7 is used as a sensor will be described.

A probe signal detected by the detecting unit 20 other than the reflected light shown in the first to the third embodiments includes a probe signal obtained by a probe placed in proximity to the sample 7 and functioning as a sensor. For such measurement using the probe, a scanning tunnel microscope, a scanning atomic force microscope (AFM), a near-field scanning optical microscope (NSOM), etc. can be used. The present invention collectively calls these microscopes the scanning probe microscope (SPM).

When the sensor placed near the specimen 7 described above is used as the detecting unit 20, the probe signal from the specimen 7 excited by the pump light 3a, probe lights 3b, 3c, etc. can be measured. When the scanning probe microscope is used, the increase of average excitation light intensity of the pump light 3a causes the increase of the signal-to-noise ratio (S/N) significantly.

Figure 8:
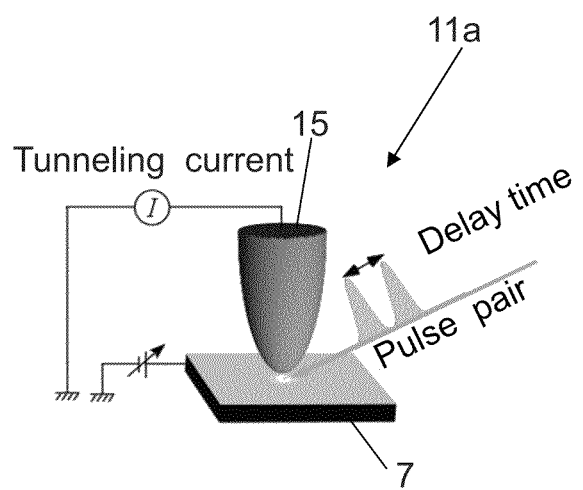
FIG. 8 is a schematic view illustrating a detection unit using a scanning tunnel microscope as a scanning probe microscope.

FIG. 8 is a schematic view illustrating a sensor 11a using a scanning tunnel microscope as the scanning probe microscope. In the sensor 11a as shown in FIG. 8, a probe 15 of the scanning tunnel microscope, which is not shown, is placed in proximity to the sample 7. A voltage is applied between the sample 7 and the probe 15 by a DC power supply 16, and a current meter 17 is connected to measure the tunneling current that flows between the sample 7 and the probe 15. As the probe 15 of the scanning tunneling microscope, a metal needle can be used. In the case of the scanning probe microscope, a sensor as the probe 15 is selected in accordance with the object to be measured.

By illuminating the sample 7 with the pulse pairs of the pump light 3a and the probe lights 3b, 3c, and measuring how dependent the probe signal, namely tunneling current, is on the delay time, the dependency of the probe signal on the delay time can be measured accurately for ultrafast phenomenon of 1 ns or faster, as in the case of the measurement of reflected light in the first to the third embodiments. By scanning the probe 15 on the surface of the sample 7, two-dimensional measurement on the surface of the sample 7 is allowed. In other words, since the excitation process and the relaxation process of the surface of the sample 7, namely the processes where the surface of the sample 7 is excited by the pump light 3a and then becomes relaxed, can be measured with high spatial resolution on the order of angstrom to nm, a delay-time-modulated scanning probe microscope having the time resolution on the order of femtosecond can be achieved.

The pump probe measuring devices 1, 30, 40 of the present invention can also be used as various measuring devices by attaching them to measuring devices such as a scanning electron microscope and a transmission electron microscope.

The present invention will hereafter be described further in detail by referring to the example as shown below.

EXAMPLE

Of the embodiments described above, the example of measurement performed using the pump probe measuring device 30 as shown in FIG. 6 will be described.

As the laser light source 3 as shown in FIG. 6, the CHAMELEON (COHERENT INC.) was used, and as the optical shutter 6c, the Pockels cell (350-80LA, CONOPTICS INC.) was used. The reflected light of the probe light focused on the sample 7 was received by the pin photodiode, and this probe signal was detected by the phase-sensitive detecting means 12, in synchronization with the periodic modulation signal of the delay time. As the phase-sensitive detecting means 12, the lock-in amplifier (SR830, Stanford Research Systems) was used.

The specifications of the optical pulse generated by the pump probe measuring device 30 are shown below.
Pulse width: 150 fs
Pulse repetition frequency: 90 MHz
$T_{d2}$: 250 ps
Delay time modulation frequency (opening/closing frequency of the shutter): 1 kHz The result of measurement performed using the pump probe measuring device 30 will then be described.

As the sample 7 to be measured, an epitaxial wafer was fabricated by growing a 1 μm-thick AlGaAs layer on a GaAs substrate and a 1 μm-thick GaAs layer on the AlGaAs layer at a temperature as low as 250° C. with use of the molecular beam epitaxy method (MBE). It is known that high-concentration defects are introduced into the GaAs layer at the growth temperature of approximately 250° C., thereby shortening the lifetime of the photocarrier significantly. The lifetime of the photocarrier is approximately several ps.

Figure 9:
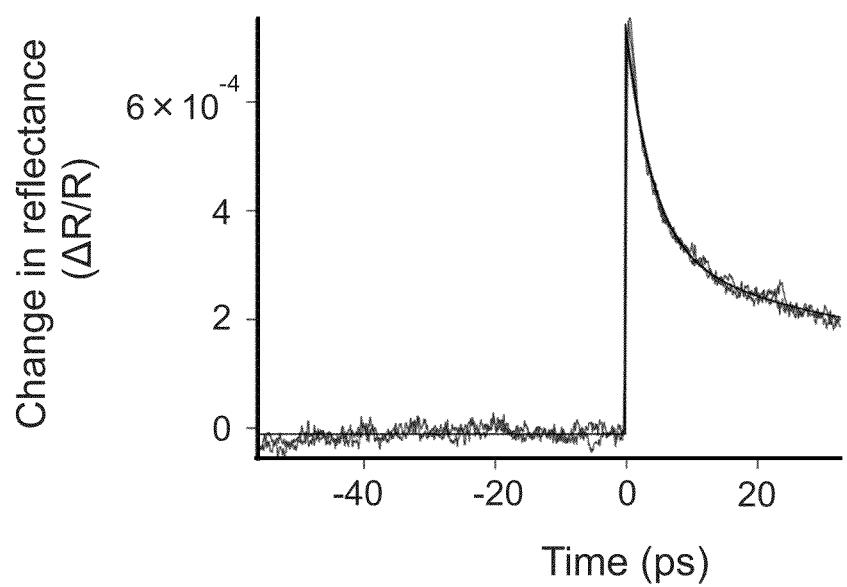
FIG. 9 is a chart showing the probe signal from the reflected light of low-temperature-grown GaAs measured by the pump probe measuring device.
Figure 10:
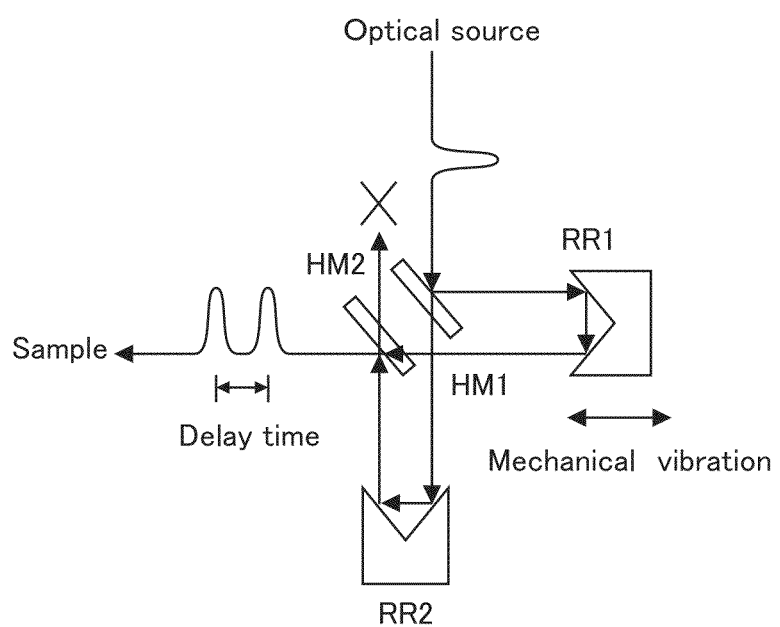
FIG. 10 is a view illustrating the configuration of a conventional delay time modulation device.
Figure 11:
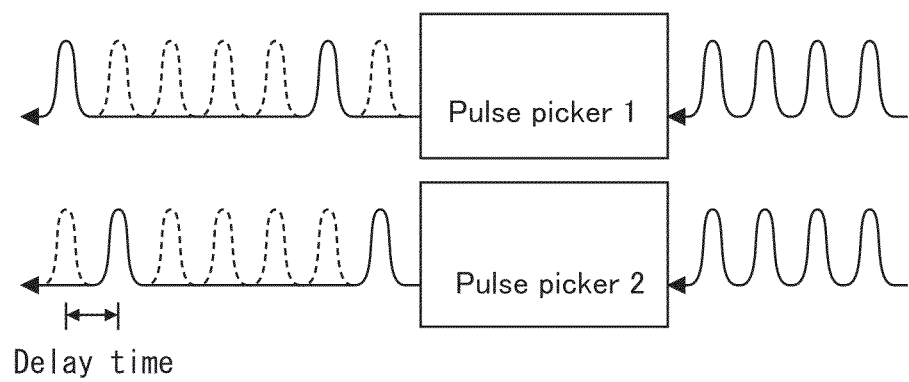
FIG. 11 is a time chart describing conventional pulse pickers.

FIG. 9 is a chart showing the probe signal from the reflected light from low-temperature-grown GaAs layer measured by the pump probe measuring device 30. The horizontal axis in FIG. 9 represents the delay time $T_{d1}$ (ps), and the vertical axis represents the value obtained by dividing the modulation amplitude of reflectance ($\Delta R = R(T_{d1}) - R(\infty)$) by the absolute value of the reflectance R.

As shown in FIG. 9, it was found that by performing the delay time modulation at the amplitude of 100 ps and frequency of 1 kHz using the pump probe measuring device 30, the process of the photocarrier excitation and that of the relaxation immediately after the excitation of the GaAs layer grown at low temperature were found to be measured on the order of ps.

The result of the measurement performed using the pump probe measuring device 30 as described above was compared with the result of measurement performed using the pump probe measuring device with pulses picked using pulse pickers (Patent Literature 1). It was found that the pump probe measuring device 30 of the present invention ensures the highly accurate delay time measurement along with the average excitation light intensity approximately 20 times higher.

The present invention is not limited to the examples described above, but various modifications are allowed within the scope of the claims of the present invention. Needless to say, they are all included in the scope of the present invention.

INDUSTRIAL APPLICABILITY

The present invention considerably improves the delay time modulation method of the delay-time-modulation-based pump probe measurement method that has thus far been used widely. Given the prospect that the use of ultrafast phenomena will take on a major significance, the scope of its application is extremely wide. The present invention is expected to be applicable in various ways including but not limited to the measurement of the carrier lifetime and transport phenomena in ps region within semiconductor nano-devices, applications in the research stages of new functional devices, and onsite applications such as the use for the evaluation of prototype devices.

What is claimed is:

1. A pump probe measuring device, comprising:
an ultrashort optical pulse laser generator that generates a first ultrashort optical pulse train which is a pump light, a second ultrashort optical pulse train which has a first delay time with respect to the pump light, and a third ultrashort optical pulse train which has a second delay time with respect to the pump light, the second and the third ultrashort optical pulse trains constitute a probe light;
an optical shutter unit to which the second and the third ultrashort optical pulse trains are introduced, the optical shutter unit emits the second and the third ultrashort optical pulse trains alternately;
an optical shutter control unit that controls the optical shutter unit;
an irradiation optical system that irradiates a sample with the pump light and the probe light;
a sensor that detects a probe signal from the sample; and
a phase-sensitive detector connected to the sensor, wherein
the irradiation optical system irradiates the sample with the first ultrashort optical pulse train as the pump light;
the second and the third ultrashort optical pulse trains are introduced into the optical shutter unit, the optical shutter unit irradiates the sample with the second and the third ultrashort optical pulse trains alternately as the probe light so that a delay time of the probe light with respect to the pump light is modulated periodically; and
the probe signal from the sample is detected by the phase sensitive detector in synchronization with the periodic modulation of the delay time.

2. The pump probe measuring device as set forth in claim 1, wherein the ultrashort optical pulse laser generator comprises:
an ultrashort optical pulse laser light source;
an optical element that divides an ultrashort optical pulse train generated by the ultrashort optical pulse laser light source into three, thereby forming the first, the second and the third ultrashort optical pulse trains;
a first optical delay unit that delays the second ultrashort optical pulse train by a first delay time with respect to the pump light; and
a second optical delay unit that delays the third ultrashort optical pulse train by a second delay time with respect to the pump light.

3. The pump probe measuring device as set forth in claim 2, wherein the first optical delay unit or the second optical delay unit comprises a movable mirror that reflects the second or third ultrashort optical pulse.

4. The pump probe measuring device as set forth in claim 1, wherein the ultrashort optical pulse laser generator comprises:
a first ultrashort optical pulse laser light source that generates the pump light;
a second ultrashort optical pulse laser light source that generates the second ultrashort optical pulse train which constitutes the probe light; and
a third ultrashort optical pulse laser light source that generates the third ultrashort optical pulse train which constitutes the probe light, wherein
the first, the second and the third ultrashort optical pulse laser light sources oscillate synchronously with specified delay times.

5. The pump probe measuring device as set forth in claim 4, wherein the device further comprises: a first optical delay unit that delays the second ultrashort optical pulse train by a first delay time with respect to the pump light; and a second optical delay unit that delays the third ultrashort optical pulse train by a second delay time with respect to the pump light.

6. The pump probe measuring device as set forth in claim 5, wherein the first optical delay unit or the second optical delay unit comprises a movable mirror that reflects the second or the third ultrashort optical pulse.

7. The pump probe measuring device as set forth in claim 1, wherein the optical shutter unit comprises: a first optical shutter; and a second optical shutter, wherein the second ultrashort optical pulse train is introduced to the first optical shutter and the third ultrashort optical pulse train is introduced to the second optical shutter.

8. The pump probe measuring device as set forth in claim 7, wherein the optical shutter unit comprises an acoustooptic modulator or an electrooptic modulator that emits the second ultrashort optical pulse train and the third ultrashort optical pulse train.

9. The pump probe measuring device as set forth in claim 1, wherein the optical shutter unit comprises: an electrooptic element; and a polarization rotation element, wherein the second ultrashort optical pulse train is introduced to the electrooptic element through the polarization rotation element, and the third ultrashort optical pulse train is introduced to the electrooptic element directly.

10. The pump probe measuring device as set forth in claim 9, wherein the electrooptic element is a Pockels cell.

11. The pump probe measuring device as set forth in claim 9, wherein the polarization rotation element is a ½ λ plate.

12. The pump probe measuring device as set forth in claim 1, wherein the sensor comprises a photodiode, a reflected light of the probe light at the sample is introduced to the photodiode, and a reflected light intensity is detected as the probe signal.

13. The pump probe measuring device as set forth in claim 1, wherein the sensor comprises a scanning probe microscope, the probe signal is detected by a probe of the scanning probe microscope on a surface of the sample on which the pump light and the probe light are focused.

14. The pump probe measuring device as set forth in claim 13, wherein the scanning probe microscope is a scanning tunnel microscope, a scanning atomic force microscope or a near-field scanning optical microscope.

15. A measuring device, comprising the pump probe measuring device as set forth in claim 1.

16. A pump probe measuring method comprising the following steps of:
    irradiating a sample with a first ultrashort optical pulse train which is a pump light;
    introducing, into an optical shutter unit, a second ultrashort optical pulse train which has a first delay time with respect to the pump light, and a third ultrashort optical pulse train which has a second delay time with respect to the pump light;
    irradiating the sample with the second ultrashort optical pulse train and the third ultrashort optical pulse train alternately as a probe light, whereby modulating a delay time of the probe light with respect to the pump light periodically; and
    detecting a probe signal with a phase-sensitive detector from the sample in synchronization with the periodic modulation of the delay time.

17. The pump probe measuring method as set forth in claim 16, comprising:
    preparing the first ultrashort optical pulse train, the second ultrashort optical pulse train and the third ultrashort optical pulse train by dividing a single ultrashort optical pulse train into three.

18. The pump probe measuring method as set forth in claim 16, comprising:
    preparing a first ultrashort optical pulse laser light source that generates the first ultrashort optical pulse train, a second ultrashort optical pulse laser light source that generates a second ultrashort optical pulse train and a third ultrashort optical pulse laser light source that generates a third ultrashort optical pulse train; wherein
    the first, the second and the third ultrashort optical pulse laser light sources oscillate and generate respectively the first, the second and the third ultrashort optical pulse trains synchronously with specified delay times.

19. The pump probe measuring method as set forth in claim 16, wherein the probe signal indicates a reflection intensity of the probe light.

20. The pump probe measuring method as set forth in claim 16, wherein the probe signal is detected by a probe of a scanning probe microscope.

* * * * *